United States Patent
Kirschbaum et al.

(10) Patent No.: US 6,653,498 B2
(45) Date of Patent: Nov. 25, 2003

(54) PROCESS FOR PREPARING OPTICALLY ACTIVE CYANOHYDRINS AND SECONDARY PRODUCTS

(75) Inventors: Bettina Kirschbaum, Frankfurt (DE); Goetz Wilbert, Gersthofen (DE); Franz Effenberger, Stuttgart (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/004,600

(22) Filed: Nov. 1, 2001

(65) Prior Publication Data

US 2002/0052523 A1 May 2, 2002

(30) Foreign Application Priority Data

Nov. 1, 2000 (DE) .......................... 100 54 011
Dec. 14, 2000 (DE) .......................... 100 62 306

(51) Int. Cl.$^7$ ...................... C07C 253/00; C07C 253/30
(52) U.S. Cl. ........................ 558/351; 435/128
(58) Field of Search ............................ 558/351; 435/128

(56) References Cited

U.S. PATENT DOCUMENTS

| 4,859,784 | A |   | 8/1989 | Effenberger et al. |         |
|-----------|---|---|--------|--------------------|---------|
| 5,346,816 | A | * | 9/1994 | Griengl et al.     | 435/128 |
| 5,350,871 | A | * | 9/1994 | Geluk et al.       | 558/351 |
| 5,885,809 | A | * | 3/1999 | Effenberger et al. | 435/128 |
| 6,225,095 | B1| * | 5/2001 | Pochlauer et al.   | 435/128 |

FOREIGN PATENT DOCUMENTS

| EP | 0 276 375 | 8/1988 |
| EP | 0 322 973 | 7/1989 |
| EP | 0 547 655 | 6/1993 |
| EP | 0 927 766 | 7/1999 |

OTHER PUBLICATIONS

English abstract for CN 1243880, Feb. 9, 2000.
Griengl H., et al., "The synthesis of chiral cyanohydrins by oxynitrilases", Trends in Biotechnology, Elsevier, 18, 6, Jun. 2000, pp. 252–256.
XP-001057697 P. Zandbergen, et al., "Synthesis of optically active cyanohydrins using almond meal", Synth. Commun., 21, 1991, 1387–1391.
XP-000993034 Von Franz Effenberger, et al., "Enzymkatalysierte Cyanhydrin–Synthese in organischen Loesungmitteln", Agnew Chem., 99, 5, 1987; pp. 491–492.
Enzyme Catalysis in Organic Synthesis, A Comprehensive Handbook, vol. 1 VCH, Weinheim, 1995, p. 22.
Michael Bauer, et al., "Kinetic Studies on the Enzyme (S)–Hydroxynitrile Lyase from *Hevea brasiliensis* Using Initial Rate Methods and Progress Curve Analysis", Biotechnology and Bioengineering, vol. 62, No. 1, Jan. 5, 1999, p. 20–29.
Franz Effenberger, "Hydroxynitrile Lyases in Stereoselective Synthesis", Stereoselective Biocatalysis, p. 321–342, 2000.

* cited by examiner

Primary Examiner—Joseph K. McKane
Assistant Examiner—Kamal Saeed
(74) Attorney, Agent, or Firm—Scott E. Hanf

(57) ABSTRACT

The present invention relates to a process for preparing optically active cyanohydrins of the formula (II),

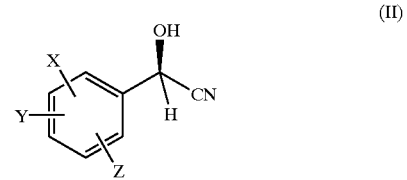

by reacting an aldehyde of the formula (I)

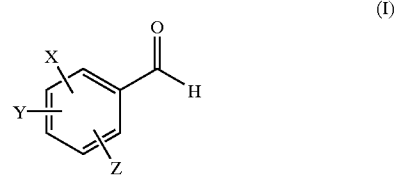

with HCN in a water-immiscible organic solvent in the presence of water, in the absence or presence of a buffer, in the presence of a (R)-hydroxynitrile lyase, where X, Y and Z in formula (II) have the same meaning as in formula (I), independently of each other are identical or different and are H, F, Cl, Br, I, OH, O($C_1$–$C_4$-alkyl), OCOCH$_3$, NHCOCH$_3$, NO$_2$ or $C_1$–$C_4$-alkyl.

14 Claims, No Drawings

PROCESS FOR PREPARING OPTICALLY ACTIVE CYANOHYDRINS AND SECONDARY PRODUCTS

BACKGROUND OF THE INVENTION

The invention relates to a process for preparing optically active cyanohydrins using a highly active (R)-hydroxynitrile lyase extract.

Optically active cyanohydrins and their secondary products, for example optically active α-hydroxycarboxylic acids, serve as building blocks for producing biologically active substances which are used in the pharmaceutical or agricultural industries, for example, as described in F. Effenberger: Hydroxynitrile Lyases in Stereoselective Synthesis (in Stereoselective Biocatalysis edited by R. N. Patel; Marcel Dekker Inc. New York—Basle 2000, pages 321 to 342).

A possible method for synthesizing optically active cyanohydrins is the use of hydroxynitrile lyase produced from natural products which, depending on the natural product, can be produced in the R or S form and converts aldehydes, in the presence of prussic acid, into the corresponding (R)- or (S)-cyanohydrins. The substrate spectrum of the enzyme differs depending on the natural product.

(R)-Hydroxynitrile lyase is most simply, and therefore most frequently, produced from almond flour.

In the sequence of aromatic aldehydes, benzaldehyde and 3- and 4-substituted benzaldehydes are included among the substrates which may be converted to optically active cyanohydrins with great success using (R)-hydroxynitrile lyase produced from almond flour as the natural product or from other natural products. In contrast, 4-hydroxybenzaldehyde and 3,4-dihydroxybenzaldehyde are among the starting materials which, using (R)-hydroxynitrile lyase produced from almond flour or other natural products may only be converted into the corresponding optically active cyanohydrins with difficulty. 2-substituted benzaldehydes are not very suitable as substrates for the reaction using (R)-hydroxynitrile lyases.

SUMMARY OF THE INVENTION

A disadvantage of the known processes is that in the reaction of the aldehydes with HCN or KCN in the presence of (R)-hydroxynitrile lyase to give the corresponding optically active cyanohydrins, the aldehydes are usually used in the form of dilute solutions of low concentration. Accordingly, the space-time yield, based on the aldehydes used, is decreased.

In view of the above-described restrictions with respect to the aldehydes to be used and the disadvantages of low space-time yields, there is a need for a process which avoids these restrictions and disadvantages and, furthermore, may also be implemented industrially in a simple manner without requiring great expenditure.

This object is surprisingly achieved by a process for preparing optically active cyanohydrins of the formula (II)

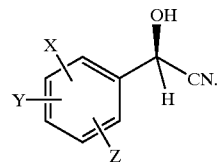

DETAILED DESCRIPTION OF THE INVENTION

It comprises reacting an aldehyde of the formula (I)

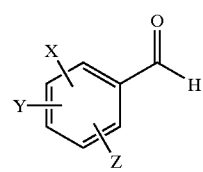

with HCN in a water-immiscible organic solvent in the presence of water, in the absence or presence of a buffer, in the presence of a (R)-hydroxynitrile lyase, where X, Y and Z in formula (II) have the same meaning as in formula (I), independently of one another are identical or different, and are H, F, Cl, Br, I, OH, O($C_1$–$C_4$-alkyl), $OCOCH_3$, $NHCOCH_3$, $NO_2$ or $C_1$–$C_4$-alkyl.

During the entire reaction with HCN, usually a pH of 0 to 8, in particular 2 to 7, preferably 3 to 6, is maintained. In a number of cases it has proved to be advantageous to maintain a pH of 3.3 to 5.5, in particular 4.0 to 5.5, preferably 4.5 to 5.3.

The reaction is usually carried out at 0 to 60° C. and intensive mixing is employed. The cyanohydrin of the formula (II) may if appropriate be converted into the corresponding carboxylic acid by hydrolysis.

The details hereinafter which also relate to a procedure using an aqueous R-hydroxynitrile lyase extract, also relate to the abovementioned procedure in the presence of an R-hydroxynitrile lyase. The procedure in the presence of the aqueous R-hydroxynitrile lyase extract mentioned below represents a special variant of the inventive process in the presence of an R-hydroxynitrile lyase. The R-hydroxynitrile lyase can be used in pure form or in the form of an extract. The R-hydroxynitrile lyase is commercially available, for example, in pure form or purified form.

The reaction is usually carried out in the presence of 20 to 1000 units of R-hydroxynitrile lyase/mmol aldehyde, in particular 50 to 500 units of R-hydroxynitrile lyase/mmol of aldehyde, preferably 80 to 400 units of R-hydroxynitrile lyase/mmol of aldehyde. The number of units of R-hydroxynitrile lyase required for reaction of the aldehyde also depends on the type of aldehyde. Readily reactive aldehydes may be reacted with relatively low numbers of units of R-hydroxynitrile lyase/mmol of aldehyde, whereas less reactive aldehydes require higher numbers of units of R-hydroxynitrile lyase/mmol of aldehyde. The units (abbreviation U) are a measure of the activity of R-hydroxynitrile lyase.

As already mentioned, the reaction is carried out in the absence or presence of a buffer. The reaction in the absence of a buffer is a particularly simple variant of the inventive process.

In a number of cases it can be advantageous to carry out the inventive reaction of the aldehyde with HCN in the presence of a buffer. Particularly suitable buffers or buffer mixtures are those which develop their buffer action in the specified pH range and maintain the pH in this range during the reaction. If the buffering action of the buffer is insufficient to maintain the pH in the predetermined range during the reaction, if necessary, the pH must be adjusted by addition of acid or addition of base.

Suitable buffers are, for example, glutamic acid-glutamate, phosphoric acid-phosphate, acetic acid-acetate and citric acid-citrate buffers, in particular acetic acid-acetate and citric acid-citrate buffer.

It has proved to be useful to carry out the reaction in the presence of 20 to 500 mmol of buffer/liter, in particular 40 to 300 mmol of buffer/liter, preferably 80 to 160 mmol of buffer/liter. Usually the buffer is dissolved in water and used in the form of an aqueous solution comprising 20 to 500, in particular 40 to 300, preferably 80 to 160, mmol of buffer per liter.

The invention, according to a particular embodiment, relates to a process for preparing optically active cyanohydrins of the formula (II)

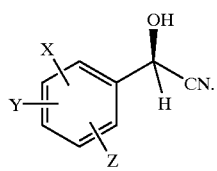

(II)

It comprises reacting, with intense mixing at 0 to 60°C., an aldehyde of the formula (I)

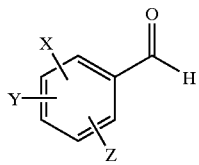

(I)

with HCN in a water-immiscible organic solvent in the presence of a (R)-hydroxynitrile lyase extract prepared by extracting a (R)-hydroxynitrile-lyase-containing natural product at pH 3.3 to 5.5 with water in the absence or presence of a buffer, separating the organic phase from the aqueous phase and if appropriate converting the cyanohydrin of the formula (II) by hydrolysis into the corresponding carboxylic acid, where X, Y and Z in formula (II) have the same meaning as in formula (I), independently of one another are identical or different and are H, F, Cl, Br, I, OH, O($C_1$–$C_4$-alkyl), OCOCH$_3$, NHCOCH$_3$, NO$_2$ or $C_1$–$C_4$-alkyl.

The inventive process makes it possible, surprisingly, to convert even less readily reactive aldehydes, such as 4-hydroxybenzaldehyde and 3,4-dihydroxy-benzaldehyde, into the optically active cyanohydrins with high yields and good ee values. Furthermore, 2-substituted benzaldehydes, for example 2-chlorobenzaldehyde, may also be highly successfully reacted by means of the inventive process to give the corresponding optically active cyanohydrins. In view of the fact that considerable difficulties would certainly be expected during a reaction of 2-substituted benzaldehydes to give optically active cyanohydrins because of the steric conditions, it is considered highly surprising that even 2-substituted benzaldehydes can be converted into the optically active cyanohydrins.

A further advantage of the inventive process is that it is possible to use the aldehydes, not only as is customary to date at comparatively low concentrations, for example 0.1 mol of aldehyde/liter, but also to carry out the reaction with considerably higher aldehyde concentrations, for example 1.0 mol of aldehyde/liter and above. Therefore, the space-time yield is also higher and achieves unexpectedly high values for enzyme reactions.

Highly successfully, in the inventive process an aldehyde of the formula (Ia)

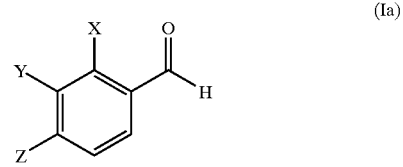

(Ia)

can be used, where X, Y and Z have the same meaning as in the abovementioned formulae (I) and (II).

In particular, an aldehyde of the formula (Ia) can be used, where X is F, Cl, Br, I, OH, O($C_1$–$C_4$-alkyl), OCOCH$_3$, NHCOCH$_3$, NO$_2$ or $C_1$–$C_4$-alkyl, in particular F, Cl, Br, OH, O($C_1$–$C_4$-alkyl) or $C_1$–$C_4$-alkyl, preferably F, Cl, OH, O($C_1$–$C_4$-alkyl) or $C_1$–$C_4$-alkyl, and Y and Z are each H, or X and Y are each H and Z is OH, or X is H and Y and Z are each OH.

An aldehyde of the formula (Ia) is of interest where X is F, Cl, OH, O($C_1$–$C_2$-alkyl) or $C_1$–$C_2$-alkyl and Y and Z are each H, or X and Y are each H and Z is OH, or X is H and Y and Z are each OH.

The reaction with HCN is carried out in a water-immiscible organic solvent. Suitable solvents for this are, in principle, all organic solvents or solvent mixtures which are inert under the reaction conditions. Those which are particularly suitable are solvents or solvent mixtures which dissolve small amounts of water, for example 0.3 to 5.0, in particular 0.5 to 3.0, preferably 0.6 to 2.5,% by weight of water, based on organic solvent.

The water-immiscible organic solvent used can be an aliphatic ether, in particular a dialkyl ether having 1 to 5, preferably 2 to 4, carbon atoms per alkyl radical, an ester of a carboxylic acid, in particular of an aliphatic carboxylic acid, having 1 to 6, in particular 1 to 4 carbon atoms, and of an aliphatic alcohol having 1 to 4, in particular 1 to 2 carbon atoms, an aliphatic ketone having in total 4 to 8, in particular 4 to 6, carbon atoms or a mixture of the same or a dilute solution of the same with a nonpolar organic solvent, for example with an aliphatic hydrocarbon having 4 to 8, in particular 4 to 6, carbon atoms, an aromatic hydrocarbon having 7 to 10, in particular 7 to 9 carbon atoms, such as toluene, ortho-, meta- and/or para-xylene, a chlorinated aliphatic or aromatic hydrocarbon such as methylene chloride, dichloroethane, trichloroethane, chloroform, chlorobenzene, dichlorobenzene and trichlorobenzene.

Very successfully, the water-immiscible solvent used can be diethyl ether, di-n-propyl ether, diisopropyl ether, methyl tert-butyl ether, di-n-butyl ether, diisobutyl ether or a mixture of the same, in particular diethyl ether, di-n-propyl ether, diisopropyl ether, methyl tert-butyl ether or a mixture of the same, preferably diisopropyl ether or methyl tert-butyl ether.

Per mol of aldehyde of the formula (I) or (Ia), 0.8 to 10.0, in particular 1.0 to 5.0, preferably 1.2 to 2.0, particularly preferably 1.3 to 1.7, mol of HCN is used. However, it is also possible to carry out the reaction at 0.5 to 20 mol of HCN/mol of aldehyde.

As already mentioned above, the reaction is carried out in the presence of an R-hydroxynitrile lyase or of an aqueous (R)-hydroxynitrile lyase extract prepared by extracting a (R)-hydroxynitrile-lyase-containing natural product at pH 3.3 to 5.5 with water in the absence or presence of a buffer.

For the sake of completeness, the preparation of the (R)-hydroxynitrile lyase extract may be considered in rather more detail at this point.

The (R)-hydroxynitrile lyase extract is made available by a process for preparing a (R)-hydroxynitrile lyase extract by extracting a (R)-hydroxynitrile-lyase-containing natural product with water in the absence or presence of a buffer at a pH of 3.3 to 5.5.

The process is a method for preparing a (R)-hydroxynitrile lyase extract which is simple and can be implemented industrially without special requirements.

The (R)-hydroxynitrile-lyase-containing natural product used very successfully is comminuted fruit cores, in particular comminuted defatted fruit cores. Fruit cores are taken to mean fruit cores and fruit stones.

According to a particularly suitable variant, the (R)-hydroxynitrile-lyase-containing natural product is comminuted defatted apple cores or almond stones. However, other (R)-hydroxynitrile-lyase-containing fruit cores or fruit stones, which are preferably comminuted and defatted, may also be used in this process.

The process, according to a preferred variant, uses defatted almond flour, as produced as waste product in the manufacture of almond oil.

The enzyme extraction is carried out at a temperature of 0 to 60° C., preferably 10 to 50° C., in particular 20 to 40° C.

As already mentioned above, the (R)-hydroxynitrile-lyase-containing natural product is extracted with water in the absence or presence of a buffer. If no buffer is employed, care must be taken to ensure that the predetermined pH of 3.3 to 5.5 is maintained during the entire reaction. This is achieved, since the pH increases to values >5.5 during the reaction, by controlled addition of acid, for example a mineral acid, during the extraction. The water used for the extraction is set in advance, also by acid addition, to an appropriate pH. Such a procedure is given in Example 5. pHs above 5.5 lead to extracts having reduced activity in the enantioselective cyanohydrin reaction, see Example 4a (comparative example).

Usually, the (R)-hydroxynitrile-lyase-containing natural product and water or aqueous buffer solution are used in a weight ratio of 1:(1 to 50), in particular 1:(2 to 20), preferably 1:(2.5 to 10).

In a number of cases it can be advantageous to carry out the extraction of the (R)-hydroxynitrile-lyase-containing natural product in the presence of a buffer. Those which are particularly suitable are buffers or buffer mixtures which develop their buffer activity in the specified pH range of 3.3 to 5.5 and maintain the pH in this range during the extraction. If the buffering action of the buffer is not sufficient to maintain the pH in the predetermined range during the extraction, the pH must be adjusted also by acid addition.

Suitable buffers are, for example, glutamic acid-glutamate, phosphoric acid-phosphate, acetic acid-acetate and citric acid-citrate buffers, in particular acetic acid-acetate and citric acid-citrate buffers.

It has proved to be useful to carry out the extraction in the presence of 20 to 500 mmol of buffer/liter, in particular 40 to 300 mmol of buffer/liter, preferably 80 to 160 mmol of buffer/liter. Usually, the buffer is dissolved in water and it is used in the form of an aqueous solution comprising 20 to 500, in particular 40 to 300, preferably 80 to 160, mmol of buffer per liter.

The extraction is particularly simple if the pH of the buffer and the amount of the buffer are chosen so as to ensure that the predetermined pH range is maintained during the entire extraction.

The natural product can also be used in non-defatted form. In this case its proportion in relation to the buffer solution must be increased in accordance with the fat content.

After an appropriate time of action of the water or the buffer solution on the natural product of, for example, 0.5 to 24, in particular 2 to 20, preferably 3 to 18, hours, the enzyme extract is usually separated from the natural product by filtration using a suitable filter apparatus.

The aqueous enzyme extract can be used together with the extracted natural product for the enantioselective HCN addition. However, it is expedient to remove the extracted natural product and to use the aqueous enzyme extract freed from the natural product. In this manner HCN-contaminated natural product is avoided as waste.

To carry out the inventive process, the aqueous phase which comprises the R-hydroxynitrile lyase or the (R)-hydroxynitrile lyase extract, is mixed intensively with the organic phase in which the aldehyde of formula (I) or (Ia) is dissolved. The HCN is distributed in accordance with the solubility both into the aqueous phase and into the organic phase. Mixing ensures that the aldehyde comes into contact with the (R)-hydroxynitrile lyase and react as desired with the HCN to form the corresponding optically active aldehyde.

The reaction, as mentioned at the outset, is carried out at 0 to 60° C., in particular at 10 to 50° C., preferably at 20 to 40° C. In many cases it has proven useful to allow the reaction to proceed at room temperature.

The aldehyde of the formula (I) or (Ia) is used at a concentration of 0.1 to 3.0, in particular 0.5 to 3.0, preferably 1.0 to 3.0, mol of aldehyde/liter. In a multiplicity of cases the reaction with HCN is carried out at an aldehyde concentration of 1.5 to 2.5 mol/liter.

During the entire reaction of the aldehyde with HCN in the presence of the R-hydroxynitrile lyase or the (R)-hydroxynitrile lyase extract, a pH of 3.3 to 5.5, in particular 4.0 to 5.5, preferably 4.5 to 5.3, is maintained, if necessary by adding acid or base.

The weight ratio of organic phase to aqueous phase (enzyme extract) is usually 20:1 to 1:20, in particular 10:1 to 1:10, preferably 5:1 to 1:5, particularly preferably 2:1 to 1:2.

After termination of the reaction the phases may be separated. The organic phase comprises the optically active cyanohydrin and in the aqueous phase is situated the (R)-hydroxynitrile lyase which can be recirculated to the reaction.

Then, if desired, the optically active cyanohydrin can be separated off from the organic phase and, if appropriate, further purified. However, the optically active cyanohydrin, if appropriate in the form of the organic phase, can also be converted into the corresponding optically active α-hydroxycarboxylic acid (α-hydroxy-phenylacetic acid= mandelic acid), for example by acid hydrolysis. For the acid hydrolysis, usually strong mineral acids are used, such as concentrated HCl or aqueous sulfuric acid. During the hydrolysis, also, good mixing of the aqueous phase in which the acid is present and the organic phase, in which the optically active cyanohydrin is situated, must be ensured.

The examples below describe the invention in more detail without restricting it.

The activities of the enzyme extracts prepared were determined by a method of M. Bauer, H. Griengl and W. Steiner Biotechnol. Bioeng. 1999, 62, 23.

The ee values of the resultant cyanohydrins were determined after derivatization with acetic anhydride/pyridine by gas chromatography on a β-cyclodextrin column. (For the definition of 1 unit, see also K. Drauz, H. Waldmann Enzyme Catalysis in Organic Synthesis, Vol. 1, Verlag Chemie, Weinheim, 1995, p. 22.)

EXAMPLES

Experimental Part

Enzyme is always taken below to mean (R)-hydroxynitrile lyase.

Example 1

Preparation of enzyme extract using 80 mmol citrate buffer/liter, pH 4.8

8.4 g of citric acid monohydrate are made up to 500 ml with demineralized water. The pH is adjusted to 4.8 with a few drops of 50% NaOH solution.

100 g of defatted almond flour are admixed with 500 ml of this citrate buffer and stirred for 16 hours at room temperature. The suspension is filtered through a glass frit. About 400 ml of aqueous enzyme extract are obtained having a pH of 5.2 and an activity of about 200 U/ml.

Preparation of (R)-2-chlorobenzaldehyde cyanohydrin 56.2 g of 2-chlorobenzaldehyde (0.4 mol) are dissolved in 200 ml of diisopropyl ether and 200 ml of the enzyme extract (40,000 U) prepared above and 16.2 g of HCN (0.6 mol) are added. The reaction mixture is stirred vigorously at room temperature for 45 min, with an emulsion being formed. After stirring is ended, about 70% of the aqueous enzyme extract originally used is separated off. It is possible to use this extract for further reactions. The organic phase contains (R)-2-chlorobenzaldehyde cyanohydrin (conversion rate according to GC 99%), having an ee of 83%.

Example 2

Preparation of enzyme extract using 80 mmol of citrate buffer/liter, pH 3.3

8.4 g of citric acid monohydrate are made up to 500 ml with demineralized water. The pH is adjusted to 3.3 using a few drops of 50% NaOH solution.

100 g of defatted almond flour are admixed with 500 ml of this citrate buffer and stirred at room temperature for 16 hours. The suspension is filtered through a glass frit. About 400 ml of aqueous enzyme extract are obtained, having a pH of 4.4 and an activity of about 75 U/ml.

Preparation of (R)-2-chlorobenzaldehyde cyanohydrin 28.1 g of 2-chlorobenzaldehyde (0.2 mol) are dissolved in 100 ml of diisopropyl ether and 270 ml of the enzyme extract (20,000 U) prepared above and 8.1 g of HCN (0.3 mol) are added. The reaction mixture is stirred vigorously at room temperature for 90 minutes, with an emulsion being formed. After stirring is ended, about 70% of the aqueous enzyme extract originally used are separated off. It is possible to use this extract for further reactions. The organic phase contains (R)-2-chlorobenz-aldehyde cyanohydrin (conversion rate according to GC 95%), having an ee of 82%.

Example 3

Preparation of enzyme extract using 160 mmol citrate buffer/liter, pH 4.8

16.8 g of citric acid monohydrate are made up to 500 ml with demineralized water. The pH is adjusted to 4.8 using a few drops of 50% NaOH solution.

100 g of defatted almond flour are admixed with 500 ml of this citrate buffer and stirred for 16 hours at room temperature. The suspension is filtered through a glass frit. About 400 ml of aqueous enzyme extract are obtained having a pH of 5.0 and an activity of about 200 U/ml.

Preparation of (R)-2-chlorobenzaldehyde cyanohydrin 28.1 g of 2-chlorobenzaldehyde (0.2 mol) are dissolved in 100 ml of diisopropyl ether and 100 ml of the enzyme extract (20,000 U) prepared above and 8.1 g of HCN (0.3 mol) are added. The reaction mixture is stirred vigorously at room temperature for 45 minutes, with an emulsion being formed. After stirring is ended, about 70% of the aqueous enzyme extract originally used is separated off. It is possible to use this extract for further reactions. The organic phase contains (R)-2-chlorobenzaldehyde cyanohydrin (conversion rate according to GC 98%), having an ee of 83%.

Example 4

Preparation of enzyme extract using 20 mmol citrate buffer/liter, pH 3.3

2.1 g of citric acid monohydrate are made up to 500 ml with demineralized water. The pH is adjusted to 3.3 using a few drops of 50% NaOH solution.

100 g of defatted almond flour are admixed with 500 ml of this citrate buffer and stirred at room temperature for 16 hours. The suspension is filtered through a glass frit. About 400 ml of aqueous enzyme extract having a pH of 5.0 and an activity of about 70 U/ml are obtained.

Preparation of (R)-2-chlorobenzaldehyde cyanohydrin 28.1 g of 2-chlorobenzaldehyde (0.2 mol) are dissolved in 100 ml of diisopropyl ether and 285 ml of the enzyme extract (20,000 U) prepared above and 8.1 g of HCN (0.3 mol) are added. The reaction mixture is stirred vigorously at room temperature for 60 minutes, with an emulsion being formed. After stirring is ended, about 70% of the aqueous enzyme extract originally used is separated off. It is possible to use this extract for further reactions. The organic phase contains (R)-2-chlorobenzaldehyde cyanohydrin (conversion rate according to GC 98%), having an ee of 83%.

Example 4a (Comparison Example)

Preparation of enzyme extract using 20 mmol citrate buffer/liter, pH 5.5 (based on the method described in Synth. Commun. 1991, 21, page 1388, but by means of extraction and removal of almond flour)

2.1 g of citric acid monohydrate are made up to 500 ml with demineralized water. The pH is set to 5.5 using a few drops of 50% NaOH solution.

100 g of defatted almond flour are admixed with 500 ml of this citrate buffer and stirred at room temperature for 16 hours. The pH increases markedly during the reaction, as demonstrated below in the case of the resultant enzyme extract. The suspension is filtered through a glass frit. About 400 ml of aqueous enzyme extract having a pH of 6.0 and an activity of about 70 U/ml are obtained.

Preparation of (R)-2-chlorobenzaldehyde cyanohydrin 28.1 g of 2-chlorobenzaldehyde (0.2 mol) are dissolved in 100 ml of diisopropyl ether and 285 ml of the enzyme extract (20,000 U) prepared above and 8.1 g of HCN (0.3 mol) are added. The reaction mixture is stirred vigorously at room temperature for 60 minutes, with an emulsion being formed. After stirring is ended, about 70% of the aqueous enzyme extract originally used is separated off. The organic phase contains (R)-2-chlorobenzaldehyde cyanohydrin (conversion rate according to GC 99%), having an ee of 55%.

The activity of the enzyme extract is, as is shown clearly by a simple comparison of the ee values (ee=enantiomeric excess) in the preparation of (R)-2-chlorobenz-aldehyde cyanohydrin in Example 4, is considerably lower than when an enzyme extract produced according to the invention is used.

Example 5

Preparation of enzyme extract using aqueous solution, pH 4.5–5.2 (without buffer)

500 ml of demineralized water are adjusted to pH 4.5 using a few ml of concentrated HCl. 100 g of defatted almond flour are admixed with this solution and stirred at room temperature for 16 hours, with the pH being maintained in a range of 4.5–5.2 by continuous addition of concentrated HCl. The suspension is filtered through a glass frit. About 400 ml of aqueous enzyme extract having a pH of 4.8 and an activity of about 200 U/ml are obtained.

Preparation of (R)-2-chlorobenzaldehyde cyanohydrin 28.1 g of 2-chlorobenzaldehyde (0.2 mol) are dissolved in 100 ml of diisopropyl ether and 100 ml of the enzyme extract (20,000 U) prepared above and 8.1 g of HCN (0.3 mol) are added. The reaction mixture is stirred vigorously at room temperature for 60 minutes, with an emulsion being formed. After stirring is ended, about 70% of the aqueous enzyme extract originally used is separated off. It is possible to use this extract for further reactions. The organic phase contains (R)-2-chlorobenzaldehyde cyanohydrin (conversion rate according to GC 99%), having an ee of 83%.

Example 6

Preparation of enzyme extract using 80 mmol citrate buffer/liter, pH 4.8 The enzyme extract is prepared as described in Example 1.

Preparation of (R)-benzaldehyde cyanohydrin 74.3 g of benzaldehyde (0.7 mol) are dissolved in 250 ml of diisopropyl ether and 100 ml of the enzyme extract (20,000 U) mentioned above and 27 g of HCN mol) are added. The reaction mixture is stirred vigorously at room temperature for 180 minutes, with an emulsion being formed. After stirring is ended, about 70% of the aqueous enzyme extract originally used is separated off. It is possible to use this extract for further reactions. The organic phase contains (R)-benzaldehyde cyanohydrin (conversion rate according to GC quantitative), having an ee of 98%.

Example 7

Preparation of enzyme extract using 80 mmol citrate buffer/liter, pH 4.8 The enzyme extract was prepared as described in Example 1.

Preparation of (R)-3-hydroxybenzaldehyde cyanohydrin 12.2 g of 3-hydroxybenzaldehyde (0.1 mol) are dissolved in 100 ml of diisopropyl ether and admixed with 100 ml of the enzyme extract (20,000 U) mentioned above and 4 g of HCN (0.15 mol). The reaction mixture is stirred vigorously at room temperature for 105 minutes, with an emulsion being formed. After stirring is ended, about 70% of the aqueous enzyme extract originally used is separated off. It is possible to use this extract for further reactions. The organic phase contains (R)-3-hydroxybenzaldehyde cyanohydrin (conversion rate according to GC 96%), having an ee of 97%.

Example 8

Preparation of enzyme extract using 80 mmol citrate buffer/liter, pH 4.8 The enzyme extract was prepared as described in Example 1. Preparation of (R)-3-hydroxybenzaldehyde cyanohydrin 48.8 g of 3-hydroxybenzaldehyde (0.4 mol) are dissolved in 200 ml of diisopropyl ether and admixed with 100 ml of the enzyme extract (20,000 U) mentioned above and 16 g of HCN (0.6 mol). The reaction mixture is stirred vigorously at room temperature for 225 minutes, with an emulsion being formed. After stirring is ended, about 70% of the aqueous enzyme extract originally used is separated off. It is possible to use this extract for further reactions. The organic phase contains (R)-3-hydroxybenzaldehyde cyanohydrin (conversion rate according to GC 94%), having an ee of 92%.

Example 9

Preparation of enzyme extract using 80 mmol citrate buffer/liter, pH 4.8 The enzyme extract was prepared as described in Example 1.

Preparation of (R)-4-hydroxybenzaldehyde cyanohydrin 12.2 g of 4-hydroxybenzaldehyde (0.1 mol) are dissolved in 100 ml of diisopropyl ether and admixed with 100 ml of the enzyme extract (20,000 U) mentioned above and 4 g of HCN (0.15 mol). The reaction mixture is stirred vigorously at room temperature for 165 minutes, with an emulsion being formed. After stirring is ended, about 70% of the aqueous enzyme extract originally used is separated off. It is possible to use this extract for further reactions. The organic phase contains (R)-4-hydroxybenzaldehyde cyanohydrin (conversion rate according to GC 70%), having an ee of 92%.

Example 9a (Comparison Example)

Preparation of enzyme extract using 80 mmol citrate buffer/liter, pH 5.3

8.4 g of citric acid monohydrate are made up to 500 ml with demineralized water. The pH is set to 5.3 using a few drops of 50% NaOH solution.

100 g of defatted almond flour are admixed with 500 ml of citrate buffer and stirred at room temperature for 16 hours. The suspension is filtered through a glass frit. About 400 ml of aqueous enzyme extract having a pH of 5.7 and an activity of about 200 U/ml are obtained.

Preparation of (R)-4-hydroxybenzaldehyde cyanohydrin 12.2 g of 4-hydroxybenzaldehyde (0.1 mol) are dissolved in 100 ml of diisopropyl ether and 100 ml of the enzyme extract (20,000 U) prepared above and 4 g of HCN (0.15 mol) are added. The reaction mixture is stirred vigorously at room temperature for 165 minutes, with an emulsion being formed. After stirring is ended, about 70% of the aqueous enzyme extract originally used is separated off. The organic phase contains (R)-4-hydroxybenzaldehyde cyanohydrin (conversion rate according to GC 63%), having an ee of 70%.

Example 10

Preparation of enzyme extract using 80 mmol citrate buffer/liter, pH 4.8 The enzyme extract was prepared as described in Example 1.

Preparation of (R)-3,4-dihydroxybenzaldehyde cyanohydrin 6.9 g of 3,4-dihydroxybenzaldehyde (0.05 mol) are dissolved in 100 ml of diisopropyl ether and 100 ml of the enzyme extract (20,000 U) mentioned above and 3 g of HCN (0.1 mol) are added. The reaction mixture is stirred vigorously at room temperature for 165 minutes, with an emulsion being formed. After stirring is ended, about 70% of the aqueous enzyme extract originally used is separated off. It is possible to use this extract for further reactions. The organic phase contains (R)-3,4-hydroxybenzaldehyde cyanohydrin (conversion rate according to GC 65%), having an ee of 76%.

Example 11

Preparation of enzyme extract using 80 mM citrate buffer:

8.4 g of citric acid monohydrate are made up to 500 ml with demineralized water. The pH is adjusted to 4.8 using a few drops of 50% NaOH solution.

100 g of defatted almond flour are admixed with 500 ml of citrate buffer and stirred at room temperature for 16 hours. The suspension is filtered through a glass frit. About 400 ml of aqueous extract having a pH of 5.2 and an activity of about 200 U/ml are obtained.

Preparation of (R)-2-chlorbenzaldehyde cyanohydrin 56.2 g of 2-chlorobenzaldehyde (0.4 mol) are dissolved in 200 ml of diisopropyl ether and 200 ml of the above-described enzyme extract (40,000 U) and 16.2 g of HCN (0.6 mol) are added. The reaction mixture is stirred vigorously at room temperature for 45 minutes, with an emulsion being formed. After stirring is ended, about 70% of the aqueous enzyme extract originally used is separated off. It is possible to use this extract for further reactions. The organic phase contains (R)-2-chlorobenzaldehyde cyanohydrin (conversion rate according to GC 99%), having an ee of 83%.

Example 12

Preparation of (R)-2-chloromandelic acid

The diisopropyl ether phase from Example 11 is admixed with 135 g of concentrated HCl and heated to 60° C. for 6 hours with good stirring. During the hydrolysis, ammonium chloride precipitates out which, after cooling, is dissolved with a little water. The phases are separated and the aqueous phase is further extracted twice, each time with 50 ml of diisopropyl ether. The combined organic phases are concentrated, the residue is taken up in 200 ml of toluene and briefly heated to boiling. On cooling, (R)-2-chloromandelic acid crystallizes out (58.2 g, 78% of theory, ee 92%).

The product can also be brought to an optical purity of >99% by further crystallization from toluene.

Example 13

Preparation of (R)-2-fluoromandelic acid In accordance with Example 11, 2-fluorobenzaldehyde (12.4 g, 0.10mol) in diisopropyl ether (50 ml) is treated with enzyme extract from Example 11 (50 ml) and HCN (4.0 g, 0.15 mol). The conversion rate after 60 min is >99%.

In accordance with Example 12, the diisopropyl ether phase is treated with concentrated HCl (35 ml). After workup, (R)-2-fluoromandelic acid (13.4 g, 81% of theory, ee 93%) is obtained.

Example 14

Preparation of (R)-2-bromomandelic acid In accordance with Example 11, 2-bromobenzaldehyde (18.5 g, 0.10 mol) in diisopropyl ether (50 ml) is treated with enzyme extract from Example 11 (50 ml) and HCN (4.0 g, 0.15 mol). The conversion after 60 min is >95%.

In accordance with Example 12, the diisopropyl ether phase is treated with concentrated HCl (35 ml). After workup, (R)-2-bromomandelic acid (15.1 g, 63% of theory, ee 91%) is obtained.

What is claimed is:

1. A process for preparing optically active cyanohydrin of the formula (II),

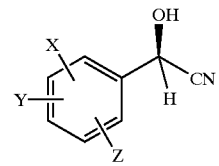

(II)

which comprises reacting an aldehyde of the formula (I)

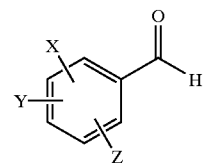

(I)

with HCN with intensive mixing at 0 to 60° C. in a water-immiscible organic solvent in the presence of an aqueous (R)-hydroxynitrile lyase extract prepared by extracting a (R)-hydroxynitrile-lyase-containing natural product of pH 3.3 to 5.5 with water in the absence of a buffer, separating the organic phase from the aqueous phase, where X, Y and Z in formula (II) have the same meaning as in formula (I), independently of each other are identical or different and are H, F, Cl, Br, I, OH, $O(C_1-C_4\text{-alkyl})$, $OCOCH_3$, $NHCOCH_3$, $NO_2$ or $C_1-C_4$-alkyl.

2. The process as claimed in claim 1, wherein a pH of 0 to 8 is maintained during the entire reaction with HCN.

3. The process as claimed in claim 1, wherein a pH of 2 to 7 is maintained during the entire reaction with HCN.

4. The process as claimed in claim 1, wherein the reaction is carried out in the presence of 20 to 1000 units of R-hydroxynitrile lyase/mmol of aldehyde.

5. The process as claimed in claim 1, wherein an aldehyde of the formula (Ia) is used

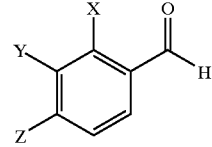

(Ia)

where X, Y and Z have the same meaning as in the abovementioned formulae (I) and (II).

6. The process as claimed in claim 1, wherein an aldehyde of the formula (Ia) is used, where X is F, Cl, Br, I, OH, O($C_1$–$C_4$-alkyl), OCOCH$_3$, NHCOCH$_3$, NO$_2$ or $C_1$–$C_4$-alkyl and Y and Z are each H, or X and Y are each H and Z is OH, or X is H and Y and Z are each OH.

7. The process as claimed in claim 1, wherein the water-immiscible solvent used is an aliphatic ether, an ester of a carboxylic acid having 1 to 6 carbon atoms and an aliphatic alcohol having 1 to 4 carbon atoms, an aliphatic ketone having a total of 4 to 8 carbon atoms or a mixture of the same or in dilution with an aliphatic hydrocarbon having 4 to 8 carbon atoms, with an aromatic hydrocarbon having 7 to 10 carbon atoms or with a chlorinated aliphatic or aromatic hydrocarbon.

8. The process as claimed in claim 1, wherein the water-immiscible solvent used is diethyl ether, di-n-propyl ether, diisopropyl ether, methyl tert-butyl ether, di-n-butyl ether, diisobutyl ether or a mixture of the same.

9. The process as claimed in claim 1, wherein the water-immiscible solvent used is diethyl ether, di-n-propyl ether, diisopropyl ether, methyl tert-butyl ether or a mixture of the same.

10. The process as claimed in claim 1, wherein 0.8 to 10 mol of HCN are used per mol of aldehyde.

11. The process as claimed in claim 1, wherein the aldehyde is used at a concentration of 0.1 to 3.0 mol of aldehyde/liter.

12. The process as claimed in claim 1, wherein a pH of 3.3 to 5.5 is maintained during the entire reaction with HCN.

13. The process as claimed in claim 1, wherein the weight ratio of organic phase to aqueous phase is 20:1 to 1:20.

14. The process as claimed in claim 1, further comprising the step of hydrolyse the cyanohydrin of the formula (II) into the corresponding carboxylic acid.

* * * * *